United States Patent [19]

Darst et al.

[11] Patent Number: 5,557,010
[45] Date of Patent: Sep. 17, 1996

[54] PREPARATION OF A 2,3-DIHALOPERFLUOROCARBONYL HALIDE

[75] Inventors: Kevin P. Darst, Lake Jackson, Tex.; Bobby R. Ezzell, Midland, Mich.; Nobuyuki Ishibe, Lake Jackson, Tex.

[73] Assignee: The Dow Chemical Company, Midland, Mich.

[21] Appl. No.: 904,748

[22] Filed: Jun. 25, 1992

[51] Int. Cl.$^6$ ..................................... C07C 51/58
[52] U.S. Cl. ........................................ 562/851; 562/859
[58] Field of Search ........................ 562/891, 859, 562/849, 840, 851, 859

[56] References Cited

U.S. PATENT DOCUMENTS

| | | | |
|---|---|---|---|
| 2,514,473 | 7/1950 | Chaney | 562/851 |
| 3,132,123 | 5/1964 | Harris, Jr. et al. | 260/87.5 |
| 3,180,895 | 4/1965 | Harris, Jr. et al. | 260/614 |
| 3,282,875 | 11/1966 | Connolly et al. | 260/29.6 |
| 3,291,843 | 12/1966 | Fritz et al. | 260/614 |
| 3,321,515 | 5/1967 | Moore et al. | 562/851 |
| 3,635,926 | 1/1972 | Gresham et al. | 260/87.5 |
| 3,725,475 | 4/1973 | Pauksch et al. | 562/859 |
| 3,943,112 | 3/1976 | Middleton | 260/80.3 |
| 4,335,255 | 6/1982 | Krespan | 560/174 |
| 4,499,249 | 2/1985 | Nakagawa et al. | 526/264 |
| 4,526,948 | 7/1985 | Resnick | 526/247 |

FOREIGN PATENT DOCUMENTS

| | | | |
|---|---|---|---|
| 163507 | of 1979 | Japan | 568/520 |
| 58-38231 | 3/1983 | Japan | 562/851 |

OTHER PUBLICATIONS

Chemical Abstract No. 92:6026j.
Chemical Abstract No. 78:16738t.
Chemical Abstract No. 69:95854t.
Chemical Abstract No. 67:99591m.
Chemical Abstract No. 97:215478a.
Derwent Abstract No. 91–053484/08.
Derwent Abstract No. 91–047261/07.
Derwent Abstract No. 89–204092/28.
Derwent Abstract No. 89–170507/23.
Derwent Abstract No. 89–204091/28.
Derwent Abstract No. 80–19243C/11.
Derwent Abstract No. 80–10263C/06.
Derwent Abstract No. 90–048050/07.
Derwent Abstract No. 90–009728/02.
Derwent Abstract No. 88–347553/49.
Derwent Abstract No. 88–079104/12.
Derwent Abstract No. 86–285955/44.
Derwent Abstract No. 85–264878/43.
Derwent Abstract No. 85–177477/29.
Derwent Abstract No. 83–784423/41.
Derwent Abstract No. 83–760123/37.
Derwent Abstract No. 82–35497E/18.
Derwent Abstract No. 81–95315D/52.
Derwent Abstract No. 81–95313D/52.
Derwent Abstract No. 81–21723D/13.
Derwent Abstract No. 80–18772C/11.
Derwent Abstract No. 68–27484Q/00.

*Primary Examiner*—James H. Reamer
*Attorney, Agent, or Firm*—John A. Langworthy

[57] ABSTRACT

Process for preparing a 2,3-dihaloperfluoropropionyl halide wherein an alkali metal chloride, bromide or iodide is contacted with a 3-haloperfluoropropene oxide in admixture in an inert liquid reaction medium.

18 Claims, No Drawings

PREPARATION OF A 2,3-DIHALOPERFLUOROCARBONYL HALIDE

FIELD OF THE INVENTION

This invention relates to a process for the preparation of a 2,3-dihaloperfluorocarbonyl halide.

BACKGROUND OF THE INVENTION

The preparation of a perfluorocarbonyl fluoride by addition of a fluoride ion to perfluoropropene oxide in gas phase is known. A process is proposed herein for the preparation of a 2,3-dihaloperfluorocarbonyl halide by addition of a halide ion to 3-haloperfluoropropene oxide in a liquid reaction medium.

SUMMARY OF THE INVENTION

This invention involves a process for preparing a 2,3-dihaloperfluoropropionyl halide wherein an alkali metal chloride, bromide or iodide is contacted with a 3haloperfluoropropene oxide in admixture in an inert liquid reaction medium, and said 2,3-dihaloperfluoropropionyl halide is recovered.

The process of this invention can be conveniently run in a liquid reaction medium, and allows for the addition to 3-haloperfluoropropene oxide of halide ions other than fluoride.

A 2,3-dihaloperfluorocarbonyl halide is useful as an intermediate in the preparation of a polymerizable haloperfluoro monomer, such as haloperfluorovinylallyl ether or 3,6-dioxa-5-halodifluoromethyl-7-haloperfluoronona-1,8-diene, either of which can be polymerized with other ethylenically unsaturated monomers such as tetrafluoroethylene or perfluorovinyloxyethanesulfonyl fluoride to prepare a thermoplastic, melt processible polymer. Such a polymer can be molded, formed or fabricated into finished articles or other goods of virtually any variety, particularly for use in the automotive and electronics industries or for the manufacture of films or membranes.

DETAILED DESCRIPTION OF THE INVENTION

A halide ion may be reacted with a 3-haloperfluoropropene oxide to produce a 2,3-dihaloperfluorocarbonyl halide. The 3-haloperfluoropropene oxide may be perfluoropropene oxide, 3-chloroperfluoropropene oxide, 3-bromoperfluoropropene oxide, or 3-iodoperfluoropropene oxide, and 3-chloroperfluoropropene oxide is preferred for this purpose. A 3-haloperfluoropropene oxide is prepared by heating the corresponding 3-haloperfluoropropene with oxygen at superatmospheric pressure in the presence of an inert diluent, as is discussed further in Carlson, U.S. Pat. No. 3,536,733, which is incorporated herein in its entirety.

The reaction of addition of a halide ion to a 3-haloperfluoropropene oxide may be represented as follows:

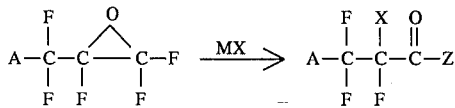

where A is a fluorine, chlorine, bromine or iodine atom; X is a chlorine, bromine or iodine atom; and Z is a fluorine, chlorine or bromine atom. "Perfluoro" as used herein means that all the hydrogen atoms on a molecule, except those whose replacement would affect the nature of the characteristic groups present, have been replaced by fluorine atoms.

A halide ion, X, from an alkali metal halide, MX (where M is an alkali metal ion), opens the 1,2 oxirane ring at the 2-carbon and adds at that position, displacing a fluorine atom from the 1-carbon. A second fluorine atom may also be displaced from the 1-carbon by the nucleophilic halide ion, X, and a mixture of both such products is typically obtained from the reaction. Z may therefore represent one of the fluorine atoms which was present on the 1-carbon in the starting material, or it may actually be X where X (except an iodide ion) has displaced that original fluorine atom.

The alkali metal ion, M, may be lithium, sodium, potassium or cesium. In general, conversion of the 3-haloperfluoropropene oxide to the corresponding 2,3-dihaloperfluoropropionyl halide decreases with the increasing size of the metal ion, although in a sulfone-based liquid reaction medium, use of sodium may give as high if not higher a percent selectivity of addition to the 2-carbon than lithium.

The alkali metal halide (MX) is admixed with an inert liquid reaction medium, being one which is non-reactive with not only the starting materials (the alkali metal halide and the propene oxide) but with the product (the propionyl halide) as well. Representative reaction media which are useful in these circumstances include aliphatic hydrocarbons such as pentane, hexane, cyclohexane, heptane or n-octane; aromatic hydrocarbons such as benzene, toluene or xylene, glycol ethers such as $R^1$—O—[—$R^3$—O—$]_a$—$R^2$, where $R^1$ and $R^2$ are each independently a $C_1$-$C_6$ hydrocarbon radical such as methyl, ethyl, isopropyl, sec-butyl, neopentyl or cyclohexyl, $R^3$ is a $C_2$-$C_6$ hydrocarbon radical such as ethyl, isopropyl, sec-butyl, neopentyl or cyclohexyl, and a is 1 to 4; and sulfones such as sulfolane (tetrahydrothiopene-1,1-dioxide), 3-methyl sulfolane, 3-sulfolene (2,5-dihydrothiopene-1,1-dioxide), dimethyl sulfone (sulfonylbismethane) and dimethyl sulfoxide. Of these, the glycol ethers and sulfones are preferred, and tetraethylene glycol dimethyl ether and sulfolane are most preferred. The liquid reaction medium may be used in an amount of about 5 moles to about 50 moles per mole of metal halide.

The liquid reaction medium is typically dried before use, for example over a molecular sieve. The alkali metal halide (MX) may be dissolved in the liquid reaction medium, or the two may be combined to form a slurry. The mixture is first heated to aid in the dispersion of the metal halide in the liquid reaction medium. The mixture is then cooled to a temperature in the range of about −10° C. to about 40° C. With agitation, a 3-haloperfluoropropene oxide is added to the reaction mixture. For this purpose it may be bubbled or dripped into the reaction vessel as appropriate according to the temperature at which the reaction is being run. Addition of the 3-haloperfluoropropene oxide at a rate of about 0.1 mole per hour to about 10 moles per hour is continued, while maintaining a temperature of about 0° C. to about 30° C. until the desired amount has been added to the reaction mixture.

The ratio of metal halide to 3-haloperfluoropropene employed in the reaction may vary from about 1.0 to about 1.3. Use of metal halide in amounts substantially greater than this results in an increase in the relative percent yield of addition of the halide ion, X, to the carbon atom at the 1-position. For example, when the ratio is about 3.0, it is not unknown for addition of the halide ion, X, to the carbon atom at the 1-position to be the dominant form of the product by as much 500 to 4,000 percent.

The reaction may be run in an open vessel at atmospheric pressure, or may be run in a closed system or under vacuum, at a pressure of 0.1 MPa to 1 MPa. The reaction may be conducted in a tank reactor, where reactants are continually entering and product is continually leaving the reaction vessel, or where each batch of reaction product is withdrawn from the vessel before another reaction is started. The reaction may also be conducted in a tubular reactor, wherein the reaction system contains multiple reaction zones.

Completion of the reaction to form the 2,3-dihaloperfluorocarbonyl halide is indicated when the reaction ceases to generate heat. The reaction mixture is allowed to warm to ambient temperature, or it may be heated, and the vessel is then evacuated by flashing under vacuum and the product is recovered by distillation. Any level of yield of the 2,3-dihaloperfluoropropionyl halide product is acceptable, but it is preferred that a yield of at least about 10 percent, and more preferably a yield of at least about 20 percent, based on the amount of 3-haloperfluoropropene oxide fed to the system, be obtained.

To illustrate the practice of this invention, examples of preferred embodiments are set forth below. It is not intended, however, that these examples should in any manner restrict the scope of this invention.

All manipulations are performed under nitrogen to exclude air and moisture. 3-Chloropentafluoropropene oxide distill the volatile products into a receiver cooled with a dry ice/acetone mixture. The distillate is analyzed by gas chromatography to obtain the relative percent yield of the 2,3-dichloroperfluoropropionyl chloride and 2,3-dichloroperfluoropropionyl fluoride products.

Fractional distillation gives more than 99 percent pure 2,3-dichlorotrifluoropropionyl fluoride with b.p. 49°–50° C. and more than 98 percent pure 2,3-dichlorotrifluoropropionyl chloride with b.p. 90°–91° C. Infrared spectra of the acid fluoride product shows the carbonyl stretching at 1,885 cm$^{-1}$ whereas those of the acid chloride exhibit it at 1,795 cm$^{-1}$. Analysis by $^{19}$F nuclear magnetic resonance of the acid fluoride shows a clear multiplex at –95 ppm (relative to trifluoroacetic acid) derived from FC=O, which is not observed in the acid chloride.

The amount of 3-chloroperfluoropropene oxide ("Oxide"), the type and amount of alkali chloride, the type and amount of liquid reaction medium ("L.R.M."), the relative percent yield of the acid fluoride and chloride products, the mass of the distillate in grams, and the isolated percent yield of the acid fluoride are shown below in Table I for Examples 1 to 10, which illustrate preparation of a 2,3-dihaloperfluoropropionyl halide by the processes of this invention.

TABLE I

| Expl. | Oxide[1] g (mole) | Alkali Chloride g (mole) | L.R.M. (ml) | Relative Yield of Acid Halide (%)[2] | | Distillate grams | Isolated % Yield of Acid Fluoride |
|---|---|---|---|---|---|---|---|
| | | | | Fluoride[3] | Chloride[4] | | |
| 1 | 18.3 (0.1) | LiCl, 5.5 (0.13) | Sulfolane (100) | 13.5 | 71.7 | 14.2 | 9.3 |
| 2 | 18.3 (0.1) | NaCl, 17.5 (0.3) | Sulfolane (100) | 49.1 | 34.8 | 7.2 | 17.7 |
| 3 | 36.6 (0.2) | KCl, 16.4 (0.22) | Sulfolane (600) | 9.4 | 67.0 | 8.0 | 1.9 |
| 4 | 18.3 (0.1) | CsCl, 50.4 (0.3) | Sulfolane (400) | 1.1 | 44.5 | 1.0 | 0.06 |
| 5 | 119 (0.65) | LiCl, 32 (0.75) | Sulfolane (1.100) | 15.0 | 82.8 | 75 | 4.0 |
| 6 | 256 (1.4) | LiCl, 64 (1.5) | Tetraglyme[5] (2,300) | 75.0 | 14.2 | 175 | 47.6 |
| 7 | 256 (1.4) | LiCl, 64 (1.5) | Tetraglyme[5] (2,200) | 78.9 | 19.9 | 206 | 58.9 |
| 8 | 138 (0.76) | LiCl, 64 (1.5) | Tetraglyme[5] (2,500) | 14.5 | 84.1 | 46 | 4.4 |
| 9 | 255 (1.4) | LiCl, 64 (1.5) | Tetraglyme[6] (2,500) | 38.1 | 6.5 | 103 | 29.8 |
| 10 | 128 (0.7) | LiCl, 32 (0.75)[7] | Tetraglyme[5] (1,100) | 77.9 | 20.6 | 99 | 59.0 |

[1]3-Chloroperfluoropropylene oxide
[2]Relative area of chromatograms
[3]2,3-Dichloroperfluoropropionyl fluoride
[4]2,3-Dichloroperfluoropropionyl chloride
[5]Tetraethylene glycol dimethyl ether
[6]Tetraethylene glycol diethyl ether
[7]Krptofix 222 (1 g) added is estimated to be 75–85 percent pure with about 10 percent 2-chloro isomer and about 5 percent 1-chloro isomer. Other reagents are dried before use; inorganic salts are dried in a vacuum oven and weighed in a dry box; solvents are dried over molecular sieve, zeolite, under nitrogen atmosphere.

EXAMPLES 1–10

Dry alkali metal chloride powder is added to an inert liquid reaction medium which is first dried over a 4A molecular sieve. The mixture is stirred under nitrogen and is cooled to a temperature of about –5° C. to about 0° C. To this slurried mixture is bubbled 3-chloroperfluoropropene oxide (80 to 90 percent pure) at a temperature of about 10° C. to about 25° C. over a period of about 0.5 to about 5 hours. One gram of [4,7,13,16,21,24-hexaoxa-1,10-diaza-bicyclo-(8.8.8)]hexacosane ("Krptofix 222"), a phase transfer agent, is also added in Example 10. The mixture is thereafter allowed to attain ambient temperature and is evacuated to

EXAMPLES 11–14

Preparation of a 2,3-dihaloperfluoropropionyl halide is also demonstrated in Examples 11 to 14, in which a metal bromide is used, as follows: Dried metal bromide powder is dispersed in an inert liquid reaction medium (L.R.M.). The metal bromide/L.R.M. mixture is stirred at 75° C. for 30 minutes. The mixture is then cooled to 40° C., and 3-chloropentafluoropropene oxide is added gradually over a 50 minute period. The temperature is maintained in a 28°40° C. range during the addition of the 3-chloropentafluoropropene oxide. After the addition of 3-chloropentafluoropropene oxide is complete, the product is isolated by heating the flask to 50° C. under 29.8 inches Hg vacuum with collection in a –78° C. cold trap.

The distilled product shows the carbonyl absorption at 1,869 cm$^{-1}$ due to the acid fluoride. $^{19}$F nuclear magnetic resonance spectrum of the distilled product exhibits a similar pattern to 2,3-dichlorotrifluoropionyl fluoride and a multiplex at –99 ppm (relative to trifluoroacetic acid).

The amount of 3-chloroperfluoropropene oxide ("Oxide"), the type and amount of alkali bromide, the type and amount of liquid reaction medium ("L.R.M."), the relative percent yield of the acid fluoride and other products, the mass of the distillate in grams, and the isolated percent yield of the acid fluoride are shown below in Table II for Examples 11 to 14.

In several exemplary runs, a haloperfluoroallylvinyl ether is polymerized with other ethylenically unsaturated monomers as follows:

RUN A

Perfluoroallylvinyl ether (25 g) and tetrafluoroethylene are separately fed into an aqueous solution (200 ml) of

TABLE II

| Expl. | Oxide[1] g (mole) | MBr g (mole) | Solvent[2] (ml) | Relative Yield[3] Fluoride3 | Relative Yield[3] Other | Distillate[4] g | Yield[5] % |
|---|---|---|---|---|---|---|---|
| 11 | 79 (0.55) | LiBr, 43 (0.5) | Sulfolane (950) | 74 | 26 | 35 | 21.4 |
| 12 | 79 (0.55) | NaBr, 154.5 (1.5) | Sulfolane (2,500) | 59 | 33 | 114 | 18.5 |
| 13 | 79 (0.55) | NaBr, 51.5 (0.5) | TGME (1,000) | 77 | 5 | 50 | 31.8 |
| 14 | 79 (0.55) | KBr, 59.5 (0.5) | Sulfolane (950) + Me Sulfolane (50) | 40.1 | 43 | 36 | 11.9 |

[1]Oxide = 3-Chloroperfluoropropylene oxide.
[2]Me Sulfolane = 3-Methylsulfolane. TGME = Tetraethylene glycol dimethyl ether.
[3]GC % area. Fluoride = 2-bromo3-chlorotrifluoropropionyl fluoride.
[4]Flash distillate from the reaction mixture.
[5]Based on the distilate quantity and the GC area %.

A 2,3-dihaloperfluorocarbonyl halide can be used to prepare a polymerizable haloperfluoro monomer such as haloperfluorovinylallyl ether. The process for preparation of a haloperfluorovinylallyl ether involves using a fluoride ion to create an alkoxide ion at the carbonyl carbon of a 2,3-dihaloperfluorocarbonyl halide, and then coupling same to additional 3-haloperfluoropropene oxide by reaction of the alkoxide ion with the epoxide ring to obtain a 2-(1',2',3'-trihaloperfluoropropoxy) -3-haloperfluoropropionyl fluoride. The 2-(1',2', 3'-trihaloperfluoropropoxy)-3-haloperfluoropropionyl fluoride can in turn be decarboxylated, using for example sodium carbonate, and can then be dehalogenated, using for example zinc, to obtain haloperfluorovinylallyl ether. If the 2-(1',2',3'-trihaloperfluoropropoxy)-3-haloperfluoropropionyl fluoride is instead treated further with fluoride ion and is then reacted with additional 3-haloperfluoropropene oxide, a coupling reaction (analogous to that by which the 2-(1',2',3'-trihaloperfluoropropoxy)-3-haloperfluoropropionyl fluoride itself is prepared) occurs, in which the product is a 2-[2'-(1",2",3"-trihaloperfluoropropoxy)-3 '-haloperfluoropropoxy]-3-haloperfluoropropionyl fluoride. If the 2-[2'-(1",2",3"-trihaloperfluoropropoxy)- 3'-haloperfluoropropoxy]-3-haloperfluoropropionyl fluoride is then decarboxylated and dehalogenated, as described above, a 3,6-dioxa-5-halodifluoromethyl-7-haloperfluoronona-1,8-diene is obtained.

An ethylenically unsaturated ether or diether, such as a haloperfluorovinylallyl ether or a 3,6-dioxa-5-halodifluoromethyl-7-haloperfluoronona-1,8-diene, can be polymerized with one or more monomers such as tetrafluoroethylene, perfluorovinyloxypropanesulfonyl fluoride, 2-chlorotetrafluoroethyl trifluorovinyl ether, or 2-fluorosulfonyltetrafluoroethyl trifluorovinyl ether, to prepare a thermoplastic, melt processible polymer. The preparation and use of a haloperfluoroallylvinyl ether or a 3,6-dioxa-5-halodifluoromethyl-7-haloperfluoronona-1,8-diene in a copolymer with another ethylenically unsaturated monomer is further described, respectively, in application Ser. No. 07/904,775, abandoned, entitled "Preparation of Haloperfluoro and Perfluoro Ethers", and application Ser. No. 07/904,774 U.S. Pat. No. 5,264,508 entitled "Polymers of Haloperfluoro and Perfluoro Ethers", each being filed on the same date as this application, assigned to the same assignee as this application, and incorporated in its entirety herein.

ammonium perfluorooctanoate (1.66 g), ammonium persulfate (0.25 g), sodium dihydrogen phosphate (1.03 g), and disodium monohydrogen phosphate (1.25 g) under nitrogen atmosphere. The pressure and temperature of the reaction mixture are kept at 150 psi and 60° C., respectively. After 25 g of tetrafluoroethylene are introduced over 150 minutes, the reaction mixture is cooled to room temperature and discharged to atmospheric pressure. Diluted hydrochloric acid (50 ml) is added to coagulate the polymer particles, which are collected by filtration. Washing with deionized water and methanol and drying under vacuum give 50 g of colorless polymer particles, which melt at 323° C. Analysis of the copolymer itself by infrared spectroscopy and Raman spectra, and analysis for a brominated polymer by X-ray photoelectron spectroscopy does not show any indication of a C=C double bond. The polymer can be readily pressed at 280° C. to give a colorless clear film which has a tear strength of 1,164 lbs/mil as determined by an Instron tensilometer.

Infrared spectra of the copolymer show no absorption at 1,800–1,850 cm$^{-1}$, but do show strong absorption at 1,155–1,365 cm$^{-1}$ for the C-F stretching and at 1,015 cm$^{-1}$ for the C-O stretching. These results suggest that the perfluoroallyl group does not remain as a pendant group on the copolymer chain. Dynamic mechanical spectroscopy of the copolymer in a 0.5 in×2 in×⅛ in molded plaque shows a sharp drop in elastic modulus at 60° C., indicating that the copolymer does not crosslink, but rather is thermoplastic.

RUN B

Tetrafluoroethylene is fed into a mixture of perfluoroallylvinyl ether (17.6 g) and perfluorovinyloxypropanesulfonyl fluoride (32.4 g) emulsified in water (300 ml), which mixture contains ammonium perfluorooctanoate (1.66 g), sodium dihydrogen phosphate (1.03 g), disodium monohydrogen phosphate (1.25 g), and ammonium persulfate (0.25 g) under nitrogen. The pressure and temperature of the reaction mixture are kept at 175 psi and 60° C., respectively. After 64 g of tetrafluoroethylene are introduced, the reaction mixture is cooled to ambient temperature (23°–26.5° C.) and is discharged to atmospheric pressure. Diluted hydrochloric acid (50 ml) is added to coagulate the copolymer particles, which are collected by filtration. Washing with deionized water and drying under vacuum gives colorless copolymer particles. The copolymer is titrated with caustic to give an equivalent weight of 1,137. The copolymer is readily pressed at 280° C. to give a colorless clear film.

In several exemplary runs, a 3,6-dioxa-5-halodifluoromethyl-7-haloperfluoronona-1,8-diene is polymerized with other ethylenically unsaturated monomers as follows:

RUN C

Tetrafluoroethylene is fed into an emulsified mixture of 3,6-dioxa-5-trifluoromethylperfluoronona-1,8-diene (2.4 g), ammonium persulfate (0.16 g), ammonium perfluorooctanoate (1.66 g), sodium dihydrogen phosphate (1.03 g) and disodium monohydrogen phosphate (1.25 g) in deionized water (300 ml). The pressure and temperature of the reaction mixture are kept at 100 psi and 60° C., respectively. After 15 g of tetrafluoroethylene are introduced over 60 minutes, the reaction mixture is cooled to ambient temperature (23.5°–26° C.) and discharged to atmospheric pressure. Diluted hydrochloric acid (50 ml) is added to coagulate the polymer particles, which are collected by filtration. Washing with deionized water and methanol and drying under vacuum gives 12 g of colorless polymer particles. The infrared spectrum of the copolymer does not show the perfluorovinyl C=C double bond absorption at 1,840 cm$^{-1}$, but does show the perfluoroallyl C=C double bond absorption at 1,800 cm$^{-1}$, indicating that the perfluorovinyl group is incorporated in the main chain of the copolymer, while the perfluoroallyl group remains as a pendant, side chain.

RUN D

2-Chlorotetrafluoroethyl trifluorovinyl ether (47 g) and 3,6-dioxa-5-trifluoromethylperfluoronona-1,8-diene (5 g) are emulsified with an aqueous mixture (300 ml) of ammonium perfluorooctanoate (1.66 g), ammonium persulfate (0.32 g), sodium dihydrogen phosphate (1.03 g), and disodium monohydrogen phosphate (1.25 g). After degassing under vacuum, tetrafluoroethylene is fed into the reaction mixture, and the pressure and temperature of the mixture are maintained at 100 psi and 60° C., respectively. After 40 g of tetrafluoroethylene are introduced over 2 hours, the reaction mixture is cooled to ambient temperature (23.5°–26° C.) and is discharged to atmospheric pressure. Diluted hydrochloric acid is added to the reaction mixture to coagulate the copolymer particles, which are collected by filtration. Washing with deionized water and drying under vacuum give 55 g of colorless copolymer particles. The infrared spectrum of the terpolymer exhibits the perfluoroallyl C=C stretching band at 1,795 cm$^{-1}$. The differential scanning calorimetry of the terpolymer shows neither exothermic nor endothermic activity from ambient temperature to 350° C., indicating that the terpolymer is amorphous.

In several exemplary runs, the copolymer prepared in Run D is cured as follows:

RUN E

A mixture of the terpolymer prepared in Run D (6 g), 1,6-diiodoperfluorohexane (0.5391 g), 2,5-dimethyl-2,5-di(tert-butylperoxy)hexane (0.3361 g), and calcium hydroxide (0.31 g) is slurried in 1,1,2-trichloro-1,2,2-trifluoroethane (150 ml). The mixture is evacuated using a rotary evaporator to strip the solvent. The dry powder obtained is placed in a mold (1.25×2.5 cm$^2$) and pressed at 175° F. The preform obtained therefrom is preheated at 350° F. for 2 minutes and is procured at the same temperature by pressing at a pressure of 5 tons for 15 minutes. The procured preform is post-cured at 450° F. for 2 hours. Dynamic mechanical properties of the cured polymer are measured with a Rheometrics Mechanical Spectrometer Model 605 in the torsional rectangular mode from −175° C. to 330° C. The storage modulus, G', of the terpolymer shows a rubbery plateau extending from a glass transition temperature at 15° C. to 340° C. The cured copolymer is transparent and possesses a rubbery resilience.

RUN F

The terpolymer prepared in Run D (6 g) and 2,5-dimethyl-2,5-di(tert-butylperoxy)hexane (0.3356 g) are added to 1,1,2-trichloro-1,2,2-trifluoroethane (150 ml). The mixture is evacuated using a rotary evaporator to give a colorless fine powder. The polymer mixture is added to a mold (1.25×2.5 cm$^2$) and is pressed at 175° F. The preform obtained thereby is preheated at 350° F. for 2 minutes and is procured at 350° F. by pressing at a pressure of 5 tons for 15 minutes. The procured preform is post-cured at 450° F. for 2 hours under nitrogen. The mechanical properties of the cured polymer are measured with a Rheometrics Mechanical Spectrometer Model 605 and show a rubbery plateau above a glass transition temperature at 15° C. to 300° C. in the storage modulus. The cured polymer is transparent and possesses a rubbery resilience.

It is within the skill in the art to practice this invention in numerous modifications and variations in light of the above teachings. It is, therefore, to be understood that changes may be made in the various described embodiments of this invention without departing from the spirit and scope of this invention as defined by the appended claims.

What is claimed is:

1. A process for preparing a 2,3-dihaloperfluoropropionyl halide by a nucleophilic addition of a chloride, bromide or iodide ion to a 3-haloperfluoropropene oxide, comprising (a) contacting an alkali metal chloride, bromide or iodide with a 3-haloperfluoropropene oxide in admixture in an inert liquid reaction medium, and (b) recovering a 2,3-dihaloperfluoropropionyl halide from said admixture.

2. The process of claim 1 wherein the 3-haloperfluoropropene oxide is perfluoropropene oxide.

3. The process of claim 1 wherein the 3-haloperfluoropropene oxide is 3-chloroperfluoropropene oxide.

4. The process of claim 1 wherein the 3-haloperfluoropropene oxide is 3-bromoperfluoropropene oxide.

5. The process of claim 1 wherein the alkali metal ion is lithium.

6. The process of claim 1 wherein the alkali metal ion is sodium.

7. The process of claim 1 wherein the alkali metal chloride, bromide or iodide is an alkali metal chloride.

8. The process of claim 1 wherein the alkali metal chloride, bromide or iodide is an alkali metal bromide.

9. The process of claim 1 wherein the inert liquid reaction medium is selected from the group consisting of a sulfone and a glycol diether.

10. The process of claim 9 wherein the liquid reaction medium is sulfolane or 3-methyl sulfolane.

11. The process of claim 9 wherein the liquid reaction medium is tetraethylene glycol dimethyl ether.

12. The process of claim 1 wherein said alkali metal chloride, bromide or iodide is contacted with said 3-haloperfluoropropene oxide at a temperature of about −10° C. to about 40° C.

13. The process of claim 1 wherein said alkali metal chloride, bromide or iodide is lithium chloride and said liquid reaction medium is tetraethylene glycol dimethyl ether.

14. The process of claim 1 wherein said alkali metal chloride, bromide or iodide is sodium chloride and said liquid reaction medium is sulfolane or 3-methyl sulfolane.

15. The process of claim 1 further comprising contacting said alkali metal chloride, bromide or iodide with said 3-haloperfluoropropene oxide until the reaction mixture ceases to generate heat.

16. The process of claim 1 wherein said alkali metal chloride, bromide or iodide is an alkali metal chloride, and said 3-haloperfluoropropene oxide is a 3-chloroperfluoropropene oxide.

17. The process of claim 1 wherein the 2,3-dihaloperfluoropropionyl halide recovered in step (b) is 2,3-dichloroperfluoropropionyl fluoride.

18. The process of claim 1 wherein the 2,3-dihaloperfluoropropionyl halide recovered in step (b) is a 2,3-dihaloperfluoropropionyl fluoride.

* * * * *